United States Patent [19]
Haar et al.

[11] Patent Number: 5,893,364
[45] Date of Patent: Apr. 13, 1999

[54] APPARATUS FOR LIGHT REFLECTION MEASUREMENTS

[75] Inventors: Hans-Peter Haar, Wiesloch; Matthias Essenpreis, Gauting; Rainer Fritsche, Brühl, all of Germany

[73] Assignee: Boehringer Mannheim GmbH, Mannheim, Germany

[21] Appl. No.: 08/752,629

[22] Filed: Nov. 19, 1996

[30] Foreign Application Priority Data

Nov. 29, 1995 [DE] Germany .................. 195 44 501.5

[51] Int. Cl.⁶ .................................................. A61B 5/00
[52] U.S. Cl. ...................... 600/310; 600/476; 356/338
[58] Field of Search .................. 600/310–317, 600/322–324, 336, 473, 474, 476, 477; 356/39–41, 337, 338; 435/4; 436/43

[56] References Cited

U.S. PATENT DOCUMENTS

| | | | |
|---|---|---|---|
| 2,706,927 | 4/1955 | Wood | 88/14 |
| 4,671,612 | 6/1987 | Sakurai et al. | 350/96.27 |
| 4,942,481 | 7/1990 | Yoshinouchi et al. | 357/471 |
| 5,030,000 | 7/1991 | Kanda | 356/40 |
| 5,052,776 | 10/1991 | Fukushima et al. | 385/120 |
| 5,077,476 | 12/1991 | Rosenthal | 600/316 |
| 5,213,105 | 5/1993 | Gratton et al. | 600/476 |
| 5,259,057 | 11/1993 | Cook | 385/120 |
| 5,284,149 | 2/1994 | Dhadwal et al. | 600/476 |
| 5,349,954 | 9/1994 | Tiemann et al. | 600/476 |
| 5,551,422 | 9/1996 | Simonsen et al. | 128/633 |
| 5,598,843 | 2/1997 | Caisey et al. | 600/476 |
| 5,638,818 | 6/1997 | Diab et al. | 600/310 |

FOREIGN PATENT DOCUMENTS

| | | |
|---|---|---|
| 0 104 772 | 4/1984 | European Pat. Off. |
| 28 23 769 | 12/1979 | Germany. |
| 29 27 814 | 1/1981 | Germany. |
| 31 13 248 | 3/1987 | Germany. |
| 38 09 084A1 | 9/1989 | Germany. |
| 91 03 974 | 8/1991 | Germany. |
| 43 14 835 | 11/1994 | Germany. |
| 0 631 137 A2 | 12/1994 | Germany. |
| 43 37 570 | 5/1995 | Germany. |
| 1-138507 | 5/1989 | Japan. |
| 2 253 070 | 8/1992 | United Kingdom. |

*Primary Examiner*—Ruth S. Smith
*Attorney, Agent, or Firm*—Nikaido, Marmelstein, Murray & Oram LLP

[57] ABSTRACT

An apparatus for light transport measurements on a test object with a measuring head which includes a contact surface for placing against an interface of the test object, light irradiation device with a light transmitter for irradiating light through the contact surface and an interface into the test object, and detection device with a light receiver for detecting light leaving the test object. The contact surface comprises at least one optically transparent light passage point for the light, on which a large number of rigid light-conducting elements are arranged, wherein an optical connection with a light transmitter or light receiver assigned to a light passage point is produced by the whole of the light-conducting elements of the light passage site.

32 Claims, 5 Drawing Sheets

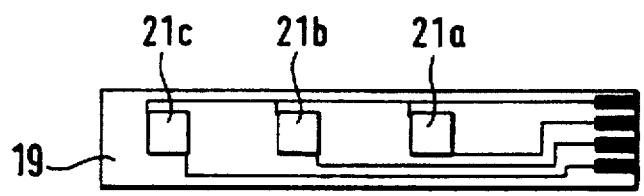
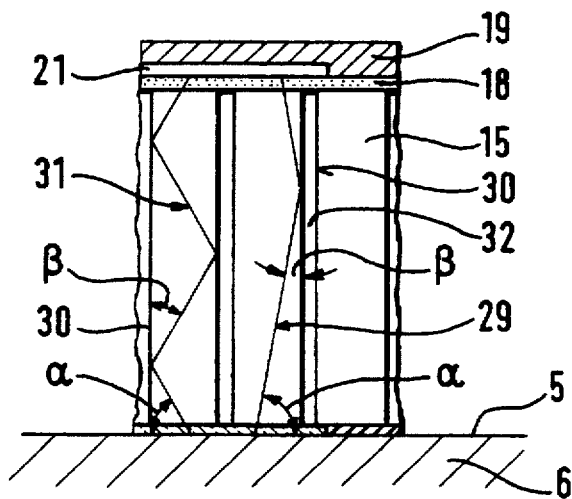
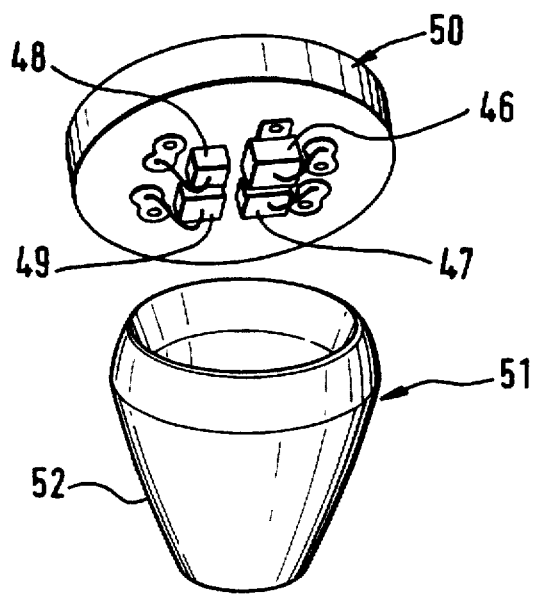

APPARATUS FOR LIGHT REFLECTION MEASUREMENTS

FIELD OF THE INVENTION

1. Background of the Invention

The invention relates to an apparatus for light transport measurements with a measuring head which comprises a contact surface for placing against an interface of the test object.

2. Description of the Related Art

A particularly important field of application is light transport measurements on test objects which scatter the light strongly, in particularly on biological tissue, above all the skin of humans or animals. Light reflection measurements on the skin are mainly performed in medical-analytical investigations. A large number of methods have been proposed in which light of varying wavelengths (from the UV at about 200 nm up to the infrared at about 2500 nm) is used. Where methods of this kind are used for the analytical determination of the concentration of substances contained in the tissue (analytes), they are generally based on the principles of spectroscopy. Examples of such methods are described in EP-0 104 772 A2 and the printed publications cited there.

A common feature of these methods is that light leaving a light transmitter ("primary light") is irradiated through the contact surface of the measuring head and an interface of the test object (in the case of the skin through its surface) into the test object and light leaving the test object through an interface after interaction with said test object ("secondary light") is detected. Thin test objects (for example the ear lobes) can be transilluminated by the light, i.e. the detection of the secondary light takes place at an interface which lies opposite the irradiation interface ("transport measurement"). A suitable light transport measuring instrument has two contact surfaces which are placed against the two opposite interfaces of the test object (cf. e.g. U.S. Pat. No. 2,706,927). The present invention can be realized on one or on both of the contact surfaces.

The invention is particularly suitable for light transport measurements in which the irradiation of the primary light and the detection of the secondary light take place at the same interface. This is commonly called a measurement "in reflection", although there is no reflection in the strict sense at the skin surface. Rather the light is also in this case irradiated into the inside of the test object where it travels from the irradiation site to a detection site, the light transport being determined by absorption and scattering in the test object. Such an apparatus can be designated as a contact reflectometer.

In recent times contact reflectometers have also been used for methods which do not operate according to spectroscopic principles. For example, in WO 94/10901 a method and a corresponding contact reflectometer are described, which permit the analysis of glucose on the basis of the scattering properties in the tissue.

The invention is suitable for but is not limited to these and similar methods. It can in general be used successfully wherever light transport measurements have to be performed in direct contact with the test object and with particularly high accuracy. Non-biological test objects for which the invention is suitable are for example test strip surfaces whose color is characteristic of a particular analyte concentration.

In order to permit the passage of the light, at least one partial area of the contact surface is optically transparent. Such a transparent section will be referred to here as the light passage site. In general separate light passage sites are provided in the contact surface for the irradiation of the primary light and for the detection of the secondary light.

The accuracy requirements of a suitable measuring device for the above-mentioned medical-analytical applications are extremely high. The total change in the secondary light as a function of the concentration of the analyte in the entire medically relevant concentration range is often only a few per cent. In order to determine the analyte concentration with sufficient accuracy from these small changes, a measuring accuracy of the reflectometer in the order of some 0.1% is required. The main concern is the stability and long-term reproducibility of the measurement. Thus it is most critical that a particular light flux of the secondary light leaving the test object leads to the same electrical signal with maximum long term accuracy (at least over several hours, if possible over several days). In many cases such devices are to be provided to patients for the individual monitoring of a critical analyte (in particular glucose). Despite the high requirements, therefore, they must be manufactured at low cost.

SUMMARY OF THE INVENTION

The invention therefore addresses the problem to improve, in the case of an apparatus with the features explained above, the measuring accuracy in particular as regards the reproducibility of the link between the secondary light flux and the measured signal.

The problem is solved for such a measuring device by the fact that the at least one light passage site in the contact surface comprises a large number of rigid light-conducting elements, wherein the whole of the light-conducting elements of a light passage site forms an optical connection with a particular light transmitter or light receiver assigned to the light passage site.

Thus the optical connection between the test object and a light receiver (detector) and/or between the test object and a light transmitter is produced in each case by a light passage site which is assigned to the respective transmitter/receiver. A plurality of light transmitters can be assigned to one light passage site, as will be explained below. In certain circumstances a plurality of receivers can also be assigned to one light passage site. This is expedient, for example, if a range of wavelength is used in which two different types of detector have to be used for different sections of the spectrum ("tandem detector").

According to the invention the primary light leaving a particular light transmitter and/or the secondary light passed to a particular light receiver (detector) at the light passage site does not pass through an unsealed opening in the contact surface and is also not transmitted by a single light-conducting element, for example a light-conducting rod, but by a large number of light-conducting elements. Preferably at least 100, particularly preferably at least 1000, light-conducting elements are provided at a light passage site, in particular at sites which are assigned to a light receiver. It is furthermore important that the light-conducting elements are rigid, i.e. no flexible light-conducting fibers shall be involved, as have been used on a large scale to date.

In the known methods the light passage sites often have very small dimensions. A point-shaped light passage site of 0.5 mm diameter can in the case of the invention nevertheless comprise over 1000, possibly even about 10000, light-conducting elements. The elements preferably have a very small cross-section of less than 0.01 $mm^2$, particularly preferably less than 0.002 $mm^2$.

Suitable light-conducting elements which are packed closely parallel to one another, and are therefore rigid despite an extremely small cross-section, are manufactured as so-called fiber optic plates.

The inventors have found that, when light-conducting elements according to the prior art are arranged between the opto-electronic converters (light transmitters and light receivers) and the test object, even extremely small mechanical changes in the sensor system or at the contact point with the interface of the test object (in particular of the skin surface) in many cases cause signal variations which are far higher than the desired measuring accuracy of about 0.1%. Therefore it is often not possible to determine the desired analytical result in the medium with sufficient accuracy or long term stability.

The invention far better ensures that always the same fraction of the photons leaving the transmitter actually passes into the test object and—with the test object unchanged—a likewise identical fraction passes to the detector after leaving the test object through the interface. The optical stability is in particular improved with respect to interference caused by minor irregularities at the surface of the test object (skin surface). At the same time the contact surface is closed, so that the interior of the measuring head is protected. Finally, the invention allows both the irradiation and the detection to be limited very precisely to particular sections of the skin surface ("irradiation site" and "detection site" as defined in WO 94/10901).

BRIEF DESCRIPTION OF THE DRAWINGS

The invention will now be explained in detail by means of embodiments shown in the figures, where FIG. 3 shows a view onto a detector arrangement, FIG. 4 shows a highly magnified and abstract representation explaining optical features critical for the invention, FIG. 6 shows a perspective view of a part of alternatively usable light irradiation means and FIG. 7 shows an exploded view of a contact surface module using a modified optical unit.

DETAILED DESCRIPTION OF THE PREFERRED EMBODIMENTS

Figure 1:
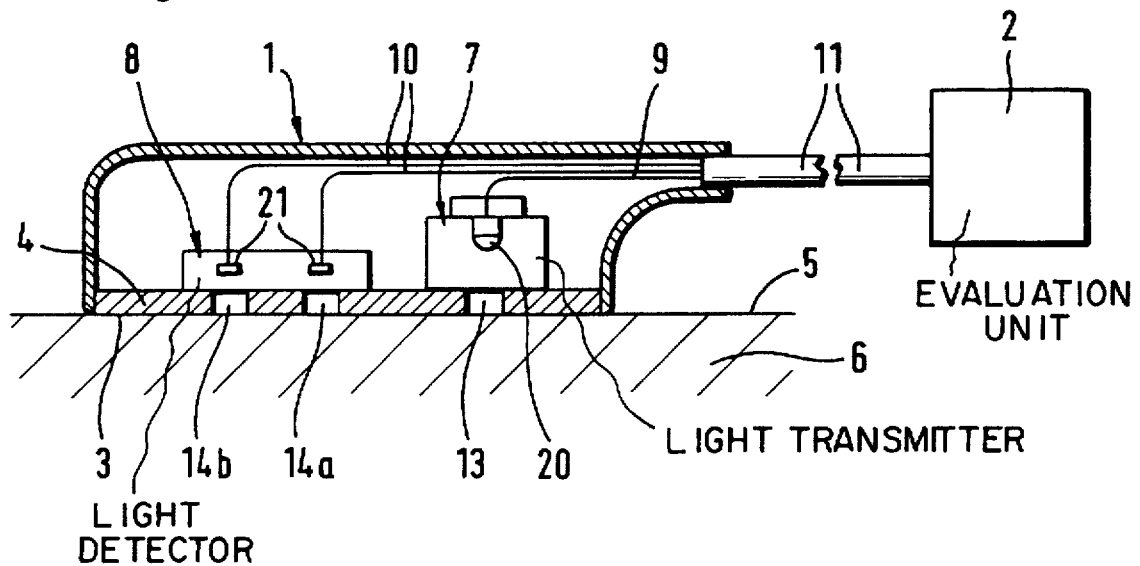
FIG. 1 shows a block diagram, partially in section, of an apparatus according to the invention.

The contact reflectometer shown in highly diagrammatic form in FIG. 1 consists essentially of a measuring head 1 and a signal processing and evaluation unit 2.

The measuring head is in contact via contact surface 3 of a sample contact plate 4 with an interface 5 of the test object 6. Light irradiation means labeled overall as 7 and detection means 8 are located in the measuring head 1. They contain a light transmitter 20 (preferably a semiconductor light transmitter, in particular a light-emitting diode) and light detectors 21 (preferably semiconductor detectors, in particular lar photodiodes, phototransistors or avalanche-type photodiodes), which are connected to the signal processing and evaluation unit 2 via electrical leads 9 and 10 and a cable 11.

For the passage of the light the contact surface 3 (and the sample contact plate 4 as a whole) comprises light passage sites, wherein in the case shown one light passage site 13 is provided for the primary light irradiated into the test object 6 and two light passage sites 14a, 14b are provided for the detection of secondary light leaving the test object 6. The position and size of the respective primary light passage site 13 (primary light passage location) and of the secondary light passage sites 14a and 14b (secondary light passage location) determines the site on the interface at which the light is irradiated into the test object ("irradiation site") or from which emerging light is detected ("detection site").

The signal processing and evaluation unit 2 contains the electronic means for activating the light irradiation means 7 and for deriving desired information concerning the inside of the test object 6 from the electrical signals (test signals) generated by the detection means 8. As already explained, the invention is suitable for a large number of such methods and the signal processing and evaluation unit 2 contains the means respectively required for this purpose and explained, for example, in the publications mentioned above. Such means generally include electronic amplifier circuits (for example a lock-in amplifier) for the analog processing of the test signal of the detection means, together with a digital signal processing unit based on a microprocessor coupled thereto.

Figure 2:
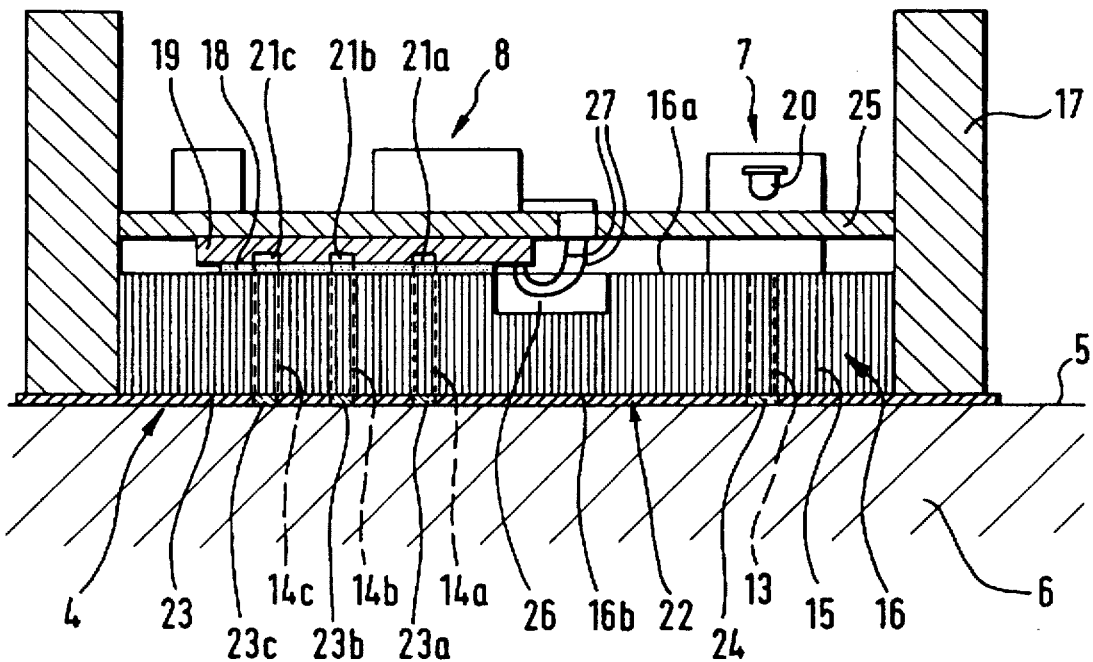
FIG. 2 shows a block diagram in cross-section of the main parts of a measuring head suitable for the invention.

FIG. 2 shows special features of the invention in highly abstract form. The contact plate 4 includes an optical fiber plate 16, which consists of a large number of closely packed, relatively short rigid light-conducting elements 15, in the form of optical fibers, running perpendicular to the contact surface 3. The length of the fibers, and hence the thickness of the optical fiber plate 16, preferably is not more than 5 mm, particularly preferably not more than 2 mm. A thickness of about 1 mm has proven particular suitable.

In the embodiment shown the optical fiber plate 16 is fitted directly between the walls of the housing 17 of the measuring head 1 in such a way that it seals off the housing 17 completely from the test object 6. It is bonded directly to a semiconductor layer 19 by means of an index-adapted adhesive 18 said layer comprising at suitable points light-sensitive areas in the form of silicon detectors 21 (photodiodes). This can be seen in overhead view in FIG. 3. In the case shown, three detectors (light receivers) 21a, 21b and 21c are provided. Recesses are provided in alignment with these detectors, namely in a mask 22 which can be located optionally on the detector-side surface 16a or the sample-side surface 16b of the optical fiber plate 16. In the shown embodiment a covering layer 23 is provided on the sample-side surface 16b, which layer forms the mask 22 and comprises at the light passage sites 14a, 14b and 14c transparent partial areas 23a, 23b, 23c of an antireflection coating, while the remaining surface consists of black paint. The mask comprises a further transparent partial area 24, which defines the light passage site 13 for the irradiation of the light.

The light irradiation means 7 and the detection means 8 are carried by a printed circuit board 25 positioned between the walls of the housing 17. A recess 26 is provided in the fiber plate 16, through which connecting wires 27 are guided, which connect the detector contacts on the silicon layer 19 with the conductors of the printed circuit board 25.

In the context of the invention it has been found that a mechanically stable construction of the optical unit is critical for the desired high measuring accuracy. Consequently a compact type of design is particularly preferred in which the following construction elements shown in FIG. 2 are realized individually or in combination with one another:

- At least the detection sites, but preferably also the irradiation sites, are provided in a single, common fiber plate 16.
- The mask 22 is connected firmly to the fiber plate. As an alternative to the coating mentioned above, a selectively black-tinted glass plate, which is bonded to the optical fiber plate 16 by mastic or by a hot melt process is also suitable as the mask and as the test-object-side seal of the fiber plate 16.
- The detectors are connected firmly and immovably to the detector-side surface 16a of the fiber plate, in particular by bonding or a similar permanent fixing method.
- The detectors 21 are arranged on a common semiconductor substrate 19. Thereby an identical characteristic curve of the detection sensitivity is obtained. Bonding of the semiconductor plate to the fiber plate in addition improves the mechanical and optical stability.

Three light-conducting elements 15 can be seen in FIG. 4 in a view which is highly magnified and not to scale. Two light beams are shown diagrammatically, wherein the light beam 29 symbolizes the path of photons which emerge at an angle $\alpha$ of virtually 90°, referred to the interface 5, and therefore impinge on the walls 30 of the light-conducting elements 15 at an acute angle $\beta$, while the light beam 31 leaves the interface 5 at a more acute angle $\alpha$, so that the angle of incidence $\beta$ of the photons on the wall 30 is greater in this case. In the invention the optical conditions of the light transmission in the light-conducting elements 15 should be such that the light is fully reflected at the walls of the light-conducting elements 15 down to very small angles of emergence $\alpha$ (i.e. up to the highest possible angles of incidence $\beta$ of the light beams on the walls 30). This property is termed the numerical aperture NA: $NA=n \cdot \sin \beta$. In technical terms the optical aperture is determined—in the case of the rigid light-conducting elements used according to the invention—by the reflection properties at the elements' walls, which in turn depend on the ratio of the refractive indices at the wall and the possible existence of an additional reflective layer on the wall. Preferably the light-conducting elements have a numerical optical aperture of more than 0.5.

The photons emerge from a strongly scattering test object 6 isotropically (i.e. uniformly distributed across a wide angular range) through the contact surface 5. As a result of the optical conditions prevailing in the invention, all these photons or at least a fraction thereof, which is constant in the long term arrive at the respective detector 21.

The light-conducting elements of a light passage site conduct the light separately from one another, and are thus essentially insulated optically from one another. If the optical insulation is incomplete, the measuring accuracy and reproducibility is affected, although perfectly good results are achieved with an optical crosstalk of less than 20%, whereas on the other hand an optical crosstalk of less than 1% can be obtained without any difficulty even with the extremely close arrangement of rigid light-conducting elements in an optical fiber plate.

The optical insulation of the light-conducting elements 15 is symbolized in FIG. 4 by gaps 32. In an actual fiber plate 16 the light-conducting elements 15 are packed far more densely than shown in FIG. 4, and the gaps 32 are therefore much smaller.

Figure 5:
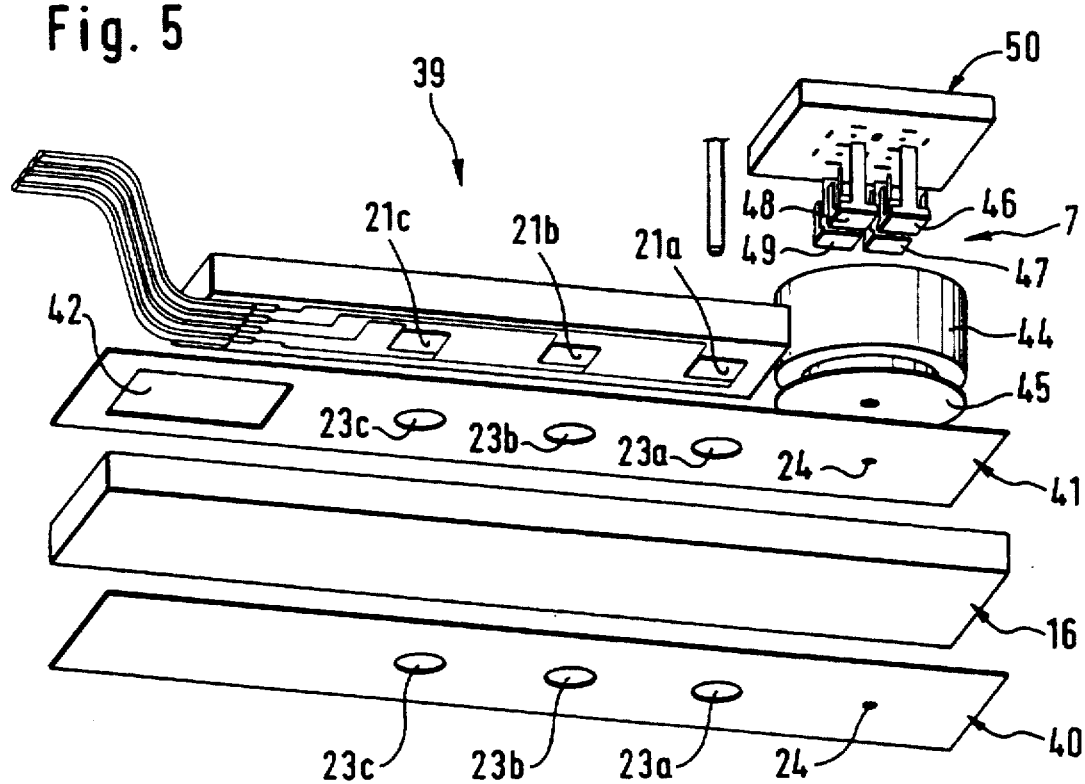
FIG. 5 shows an exploded view of the optical unit of a contact surface module for the invention.

In the optical unit 39 shown in FIG. 5 which forms a part of a contact surface module and which is suitable in particular for analytical investigations of human skin, an optical fiber plate 16 is sandwiched between two masks 40, 41, wherein both masks 40, 41 comprise at the same points of the surface of the fiber plate 16 (therefore in alignment with one another), transparent partial areas 23a, 23b, 23c for detectors 21a, 21b, 21c, and a transparent partial area 24 for the irradiation of light. The masks 40, 41 can consist of black ink which is applied by screen-printing. Particularly preferably a photosensitive layer is used for the mask, in which the optical openings are produced by an exposure process (as with the manufacture of semiconductor boards). This method can be easily incorporated in the manufacturing process. No change of the production tool is necessary after generating the mask layer. Therefore, precise assembly is facilitated.

The use of two masks on both sides of the fiber plate 16 is advantageous. The mask on the detector-side surface 16a of the fiber plate 16 can be generated with particular high precision and this method step can be incorporated in the manufacturing process as described. On the other hand a dark mask on the sample-side surface 16b of the fiber plate 16 is often also advantageous—irrespective of the precise position of the light passage sites—in order to absorb light components which leave the sample surface between the irradiation and detection sites. Such a mask can be produced with slightly less precision and be applied for example by a printing method.

In FIG. 5 the detector-side fiber plate 41 comprises an additional recess 42 for accommodating the electrical wiring for the connection between the detectors 21a, 21b, 21c and the measurement electronics.

In the embodiment shown in FIG. 5 the light irradiation means 7 are so constructed that light of a plurality of different wavelengths can be irradiated at a single point in the test object which is defined by the transparent point 24 in the masks 40, 41. To this end four light-emitting diodes 46 to 48 are arranged within an Ulbricht cylinder 44, which is closed in a downward direction (towards the fiber plate 16) by a layer 45 silvered on its inside. The light emitting diodes radiate light of different wavelengths and are secured to a covering plate 50 closing the Ulbricht cylinder in an upward direction.

Instead of the Ulbricht cylinder 44 another optical element can be used, which causes the light from the various light-emitting diodes 46 to 49 to impinge as isotropically as possible at the same point on the surface of the fiber plate 16. An optical element of this kind is termed a "beam combiner". Preferably a beam-combiner element suitable for the invention should comprise an optical cavity whose walls reflect (diffusely or specularly), so that the light emerging from light transmitters which are attached at various points on the walls of the cavity is distributed isotropically in the cavity.

The dimensions of the cavity in relation to the maximum light exit distance (distance between the light exit points furthest from one another) of the light transmitters are important for a sufficiently isotropic light distribution. Preferably the minimum distance of the light transmitters from the light exit opening of the beam-combiner element (i.e. from the light entry opening of the assigned light passage site) should be three times as great and the minimum mean diameter of the cavity should be at least twice as great as the maximum light exit distance. The optical cavity of the beam-combiner element does not necessarily have to be empty. For example, a truncated-cone-shaped component of a transparent plastics material is suitable, which forms a conical light conductor 51 that is silvered on its generated surface 52 in order to achieve a diffusion effect. A beam combiner of this kind is shown in FIG. 6.

The embodiment shown in FIG. 5 with one light passage site for the primary light and a plurality of light passage sites for the secondary light makes it possible to determine the reflection properties of a test object for several different test distances between the respective irradiation site of the primary light and the respective detection site of the secondary light. This is advantageous in particular with investigations in which not only the optical absorption behaviour (absorption coefficient $\mu_a$), but also the scattering behaviour of the test object (scattering coefficient $\mu_s$) is to be investigated. Such methods are described in the international patent applications WO 94/10901, WO 95/12348 and WO 95/32416. It can alternatively also be advantageous to work with a plurality of irradiation sites and only one detection site or with a combination of several irradiation and several detection sites.

Figure 7:
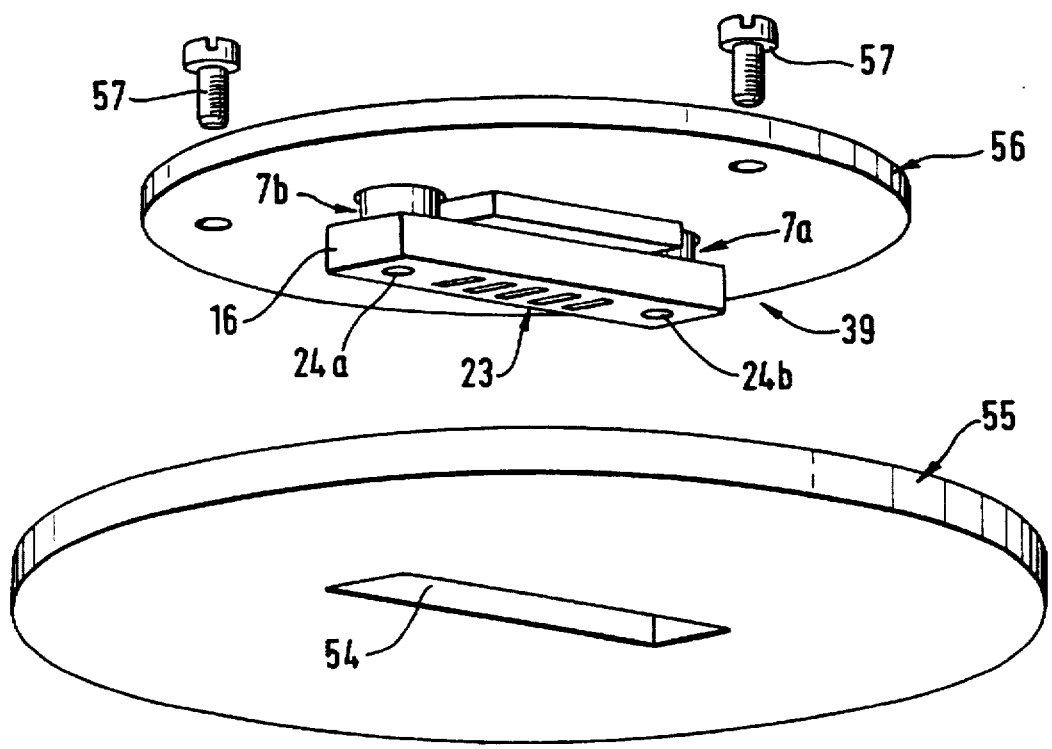

In the contact plate module shown in FIG. 7 the optical unit 39 comprises for example two beam combiners as part of the light irradiation means 7a, 7b. Two transparent areas 24a, 24b are provided accordingly for the primary light on the underside of the fiber plate 16, which define two different irradiation sites on the skin surface. In addition five transparent areas 23 are provided for the detection, corresponding to five different detection sites on the skin surface.

FIG. 7 shows furthermore a suitable structural arrangement in which the fiber plate 16 is located in a corresponding recess 54 in a skin contact plate 55, which preferably is made from metal or glass. Such an arrangement, in which only a part of the skin contact plate consists of an optical fiber plate, is advantageous with respect to the cost. For example, the optical unit 39 may be connected as shown to the skin contact plate 54 in a firm and stable manner by means of a holding plate 56 and screws 57.

In the embodiment of FIG. 7 two light sources (light irradiation means 7a and 7b) are assembled together with a plurality of detectors to a common optical fiber plate 16. The invention allows configurations of this kind with a plurality of irradiation sites and a plurality of detection sites which are of particularly compact design and simultaneously excellent measuring accuracy. In this way a chessboard-type arrangement of many irradiation sites and detection sites is possible with a relatively simple design.

Figure 8:
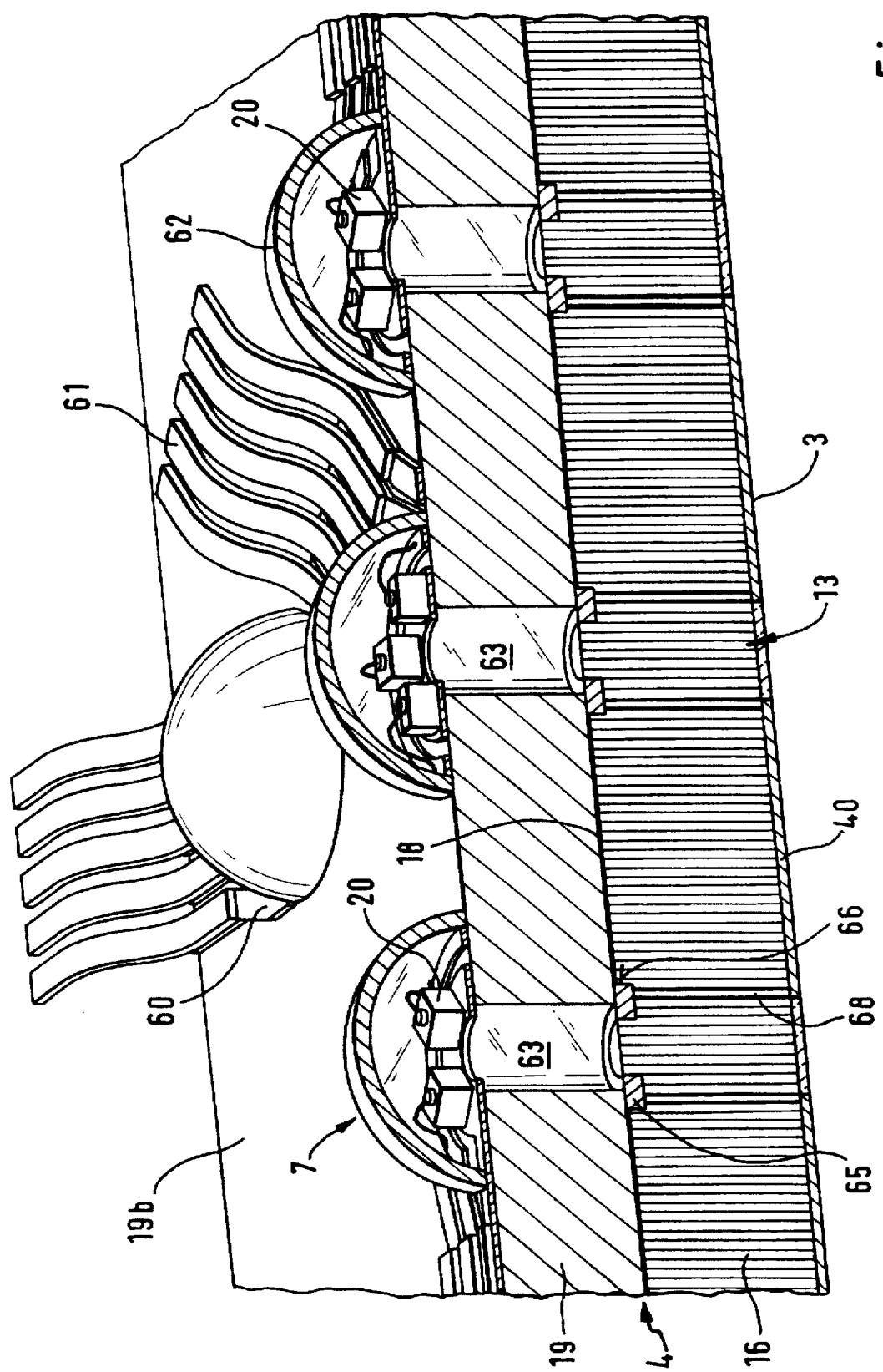
FIG. 8 shows a cut-out view—partially in section and partially in perspective—of a further embodiment of the contact surface module.
Figure 9:
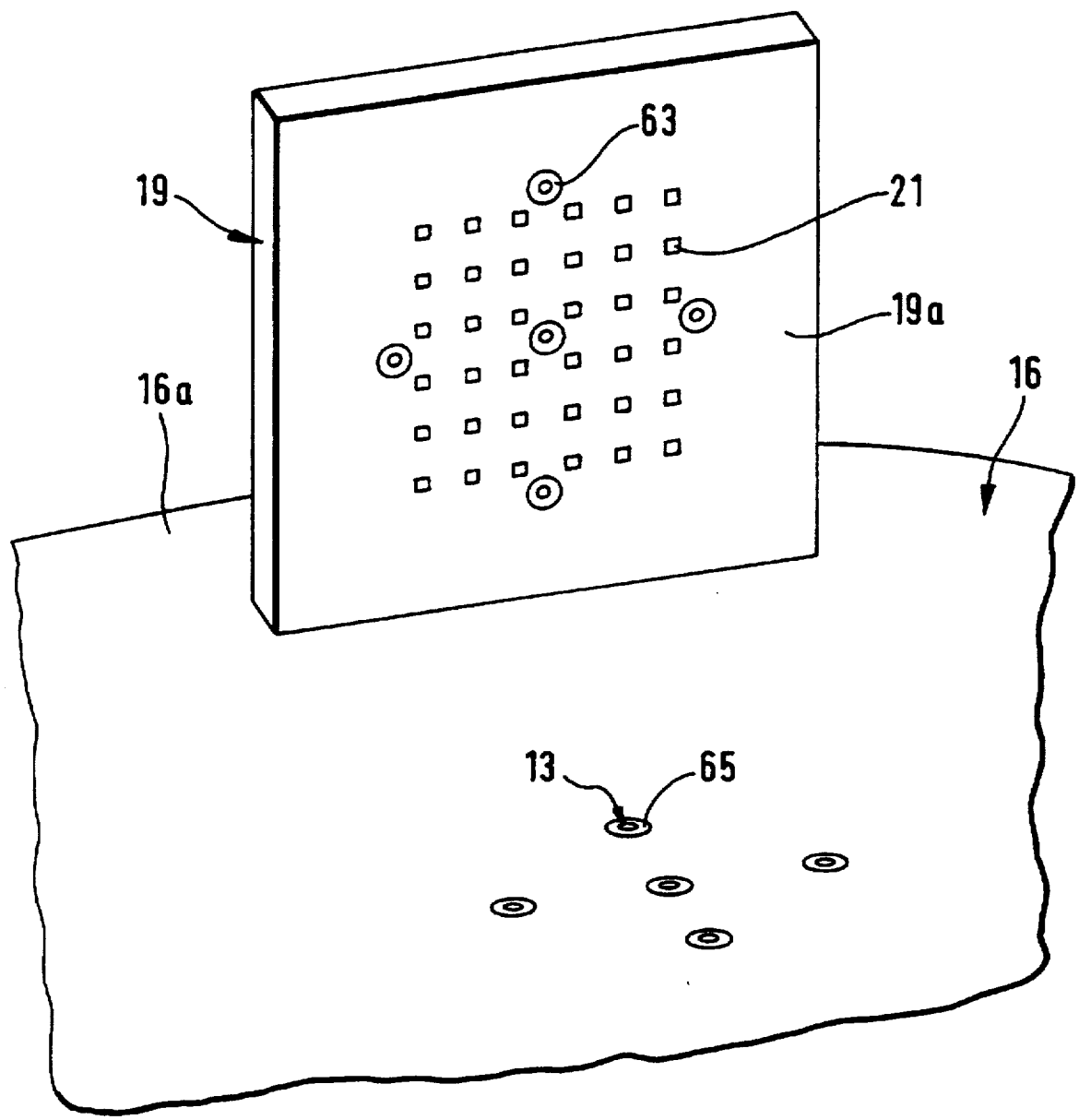
FIG. 9 shows a perspective view of the contact surface module of FIG. 8 in which the semi-conductor layer is shown in upright position to make its underside visible.

Such an embodiment is shown in FIGS. 8 and 9 which also show further preferred embodiments which can be used individually or in combination.

FIG. 8 shows a cout-out of a sample contact plate 4 which consists of an optical fiber plate 16 and a silicon semiconductor layer 19 which is bonded to fiber plate 16 by means of a layer 18 of index-adapted adhesive. As in FIG. 2, detectors 21 are integrated into semi-conducting layer 19. A plurality of detectors 21 (in this case 6×6 detectors having a surface area of 0.25×0.25 mm each) are arranged on the underside 19a of layer 19 in a chessboard-type arrangement having a dimension of 10 mm.

In this embodiment also light-transmitters 20 are fixed to semi-conducting substrate 19, namely by bonding to its upper surface 19b. They are contacted by a wirebond-method and connected via thin layer leads 60 and contacts 61 to the signal processing and evaluation unit 2. In a similar manner as in the embodiment of FIG. 5 and 6, a plurality of light-transmitters of different wavelengths—embodied as light-emitting diodes—are provided for each light passage site 13 of the primary light. These radiate the light essentially sidewards and upwards. Isotropical irradiation is accomplished by means of a beam combiner element 62. The optical cavity of the beam combiner is in this case closed by a reflecting dome-shaped cover.

At each light passage site 13 for the primary light, a light passage channel 63 between the surfaces of silicon layer 19 is provided via which the primary light travels to the light passage site 13. The inner surface of channel 63 is light-reflecting by means of a metallization. Alternatively, also a light-guiding rod which is inserted into a bore of a silicon layer could be used. In this case, the inner side of the bore should have a light-absorbing coating.

A further special feature of the embodiment shown refers to the fact that at each light passage site a surface-light barrier 65 is provided. It is formed by an optical locking ditch. This is a ring-shaped groove which is provided (for example by engraving) in the upper surface of fiber plate 16, the depression being preferably filled with an optically absorbing substance. Thereby, optical cross-talk of the primary light at the surface of fiber plate 16 is eliminated.

With such optical light barriers 65 no mask on the upper surface of fiber plate 16 is necessary whereas on the skin-side of fiber plate 16 a mask 40 should preferably be present.

As a further means for minimizing any remaining optical cross-talk inside fiber plate 16, a jacket 68 surrounding light passage site 13 and consisting of an absorbing substance is provided which perferably has a cylindrical shape. For example, during the production of fiber plate 16, glass fibers of black color can be incorporated to form the jacket surface surrounding the light passage site.

We claim:

1. An apparatus for light transport measurements on a test object for generating medical analysis data on a concentration of an analyte in the test object, said apparatus comprising:

a measuring head, said measuring head including a contact surface for contacting an interface of the test object;

at least one light irradiation means connected to the measuring head for irradiating primary light into the test object through the contact surface and the interface, said irradiation means comprising a light transmitter;

at least one detection means connected to the measuring head for detecting secondary light emerging from the test object through the interface and the contact surface, said detection means comprising a light receiver; and a signal processing unit connected to the detection means for processing a signal which is output by the detection means to yield an analytical result, wherein said analytical result corresponds to the concentration of the analyte in the test object, wherein said contact surface includes at least one optically transparent primary light passage means for conducting light therethrough from said light transmitter to which it is optically connected, and at least one optically transparent secondary light passage means for conducting light therethrough to said light receiver to which it is optically connected, wherein a size and position of a site on the interface at which the light is irradiated into the test object and a site on the interface at which the light emerging from the test object is detected are determined by a position and size of the at least one primary light passage means and the at least one secondary light passage means, wherein at least one of said primary light passage means and said secondary light passage means comprises at least 100 rigid light-conducting elements which together conduct the light from the light transmitter or to the light receiver to which the light passage means is connected, and wherein light from the secondary light passage means is used to provide input to the signal processing unit to generate medical analysis data regarding said concentration of the analyte in the test object.

2. An apparatus according to claim 1, wherein said at least one light passage means comprises at least 1000 light conducting elements.

3. An apparatus according to claim 1, wherein each of said plurality of light conducting elements has a cross-section which is less than 0.01 mm$^2$.

4. An apparatus according to claim 1, wherein each of said plurality of light conducting elements has a cross-section which is less than 0.002 mm$^2$.

5. An apparatus according to claim 1, wherein the light conducting elements have a numerical aperture of greater than 0.5.

6. An apparatus according to claim 1, wherein a length of said light conducting elements is at most 5 mm.

7. An apparatus according to claim 1, wherein a length of said light conducting elements is at most 2 mm.

8. An apparatus for light transport measurements on a test object, said apparatus comprising:

a measuring head, said measuring head including a contact surface for contacting an interface of the test object;

at least one light irradiation means connected to the measuring head for irradiating primary light into the test object through the contact surface and the interface, said irradiation means comprising a light transmitter;

at least one detection means connected to the measuring head for detecting secondary light emerging from the test object through the interface and the contact surface, said detection means comprising a light receiver;

wherein said contact surface includes at least one optically transparent light passage means, said at least one optically transparent light passage means for conducting light therethrough from said at least one light irradiation means or to said at least one detection means, to which it is optically connected, said at least one light passage means comprising a plurality of rigid light-conducting elements which together conduct the light of the light irradiation means or light detection means to which the light passage means is connected, and wherein the plurality of light-conducting elements comprise a plurality of optical fibers disposed in parallel, and connected with each other to form a plate, said plate being disposed adjacent the contact surface.

9. An apparatus according to claim 8, wherein a plurality of separate plate light passage means are provided in the plate.

10. An apparatus according to claim 9, wherein said plate includes a first plate light passage means of said plurality of plate light passage means and a second plate light passage means of the plurality of plate light passage means, said first and second plate light passage means being separated by a surface light barrier.

11. An apparatus according to claim 9, wherein at least one of said plurality of plate light passage means is surrounded by an optically absorbing jacket.

12. An apparatus according to claim 9, wherein the light receiver of the detection means is disposed upon and connected to a detector-side surface of the plate, said detector side surface being opposite to a contact surface side at the plate.

13. An apparatus according to claim 12, further comprising a plurality of detection means, each detection means of said plurality of detection means comprising a light receiver, and wherein the light receivers are disposed on a common semiconductor substrate, and are connected to the detector-side surface of the plate.

14. An apparatus according to claim 13, wherein the semiconductor substrate comprises a light passage channel therein, and wherein light of the light transmitter is irradiated into the test object via the light passage channel.

15. An apparatus according to claim 9, further comprising a mask on at least one side of the plate.

16. An apparatus according to claim 8, where said at least one light irradiation means comprises a plurality of light transmitters, said plurality of light transmitters radiating light having different wavelengths, wherein primary light from the light transmitters is combined by a beam-combiner element operatively connected to said light transmitters to irradiate a common site on a side of the plate which is opposite to a side of the plate which faces the contact surface.

17. An apparatus according to claim 16, wherein said beam combiner element includes an optical cavity therein, said optical cavity surrounding said light transmitters and having walls which reflect light impinging thereupon.

18. An apparatus according to claim 8, wherein said at least one light passage means comprises at least 100 light conducting elements.

19. An apparatus according to claim 8, wherein said at least one light passage means comprises at least 1000 light conducting elements.

20. An apparatus according to claim 8, wherein each of said plurality of light conducting elements has a cross-section which is less than 0.01 mm$^2$.

21. An apparatus according to claim 8, wherein each of said plurality of light conducting elements has a cross-section which is less than 0.002 mm$^2$.

22. An apparatus according to claim 8, wherein the light conducting elements have a numerical aperture of greater than 0.5.

23. An apparatus according to claim 8, further comprising a signal processing unit connected to the at least one detection means for processing a signal which is output by the detection means to yield an analytical result, wherein said analytical result corresponds to a concentration of a substance in the test object.

24. An apparatus for light transport measurements on a test object, said apparatus comprising:

a measuring head, said measuring head including a contact surface for contacting an interface of the test object;

at least one light irradiation means connected to the measuring head for irradiating primary light into the test object through the contact surface and the interface, said irradiation means comprising a light transmitter;

at least one detection means connected to the measuring head for detecting secondary light emerging from the test object through the interface and the contact surface, said detection means comprising a light receiver;

wherein said contact surface includes at least one optically transparent light passage means, said at least one optically transparent light passage means for conducting light therethrough from said at least one light irradiation means to which it is optically connected, said at least one light passage means comprising a plurality of rigid light-conducting elements which together conduct input light to the light irradiation means to which the light passage means is connected, wherein said at least one light irradiation means comprises a plurality of light transmitters, said plurality of light transmitters radiating light having different wavelengths, wherein the primary light from the light transmitters is combined by a beam-combiner element operatively connected to said light transmitters to irradiate said at least one light passage means.

25. An apparatus according to claim 24, wherein said beam combiner element includes an optical cavity therein, said optical cavity surrounding said light transmitters and having walls which reflect light impinging thereupon.

26. An apparatus according to claim 24, further comprising a signal processing unit connected to the at least one detection means for processing a signal which is output by the detection means to yield an analytical result, wherein said analytical result corresponds to a concentration of a substance in the test object.

27. An apparatus according to claim 24, wherein said at least one light passage means is surrounded by an optically absorbing jacket.

28. An apparatus according to claim 24, wherein said at least one light passage means comprises at least 100 light conducting elements.

29. An apparatus according to claim 24, wherein said at least one light passage means comprises at least 1000 light conducting elements.

30. An apparatus according to claim 24, wherein each of said plurality of light conducting elements has a cross-section which is less than 0.01 $mm^2$.

31. An apparatus according to claim 24, wherein each of said plurality of light conducting elements has a cross-section which is less than 0.002 $mm^2$.

32. An apparatus according to claim 24, wherein the light conducting elements have a numerical aperture of greater than 0.5.

* * * * *